United States Patent [19]

Wilbur et al.

[11] Patent Number: 4,885,153

[45] Date of Patent: Dec. 5, 1989

[54] RADIOHALOGENATED PROTEINS

[75] Inventors: Daniel S. Wilbur; Alan R. Fritzberg, both of Edmonds; David S. Jones, Seattle, all of Wash.

[73] Assignee: Neorx Corporation, Wash.

[21] Appl. No.: 338,497

[22] Filed: Apr. 13, 1989

Related U.S. Application Data

[63] Continuation of Ser. No. 852,740, Apr. 21, 1986, abandoned, which is a continuation-in-part of Ser. No. 735,392, May 17, 1985, abandoned.

[51] Int. Cl.$^4$ .................. A61K 49/02; A61K 43/00; A61K 39/395
[52] U.S. Cl. ........................... 424/1.1; 424/9; 530/388; 530/402
[58] Field of Search .............. 424/1.1, 9; 530/387, 530/389, 388, 402; 436/547

[56] References Cited

U.S. PATENT DOCUMENTS

| | | | |
|---|---|---|---|
| 3,979,506 | 9/1976 | Smith | 424/1.1 |
| 4,279,887 | 7/1981 | Baldwin et al. | 424/1.1 |
| 4,284,619 | 8/1981 | Lin | 424/1.1 |
| 4,331,647 | 5/1982 | Goldenberg . | |
| 4,381,292 | 4/1983 | Bieber et al. | 424/1.1 |
| 4,421,735 | 12/1983 | Hager et al. | 424/1.1 |
| 4,450,149 | 5/1984 | Kabalka . | |
| 4,473,544 | 9/1984 | Machulla et al. | 423/1.1 |
| 4,528,177 | 7/1985 | Molloy et al. | 424/1.1 |
| 4,659,839 | 4/1987 | Nicollotti et al. | 424/1.1 X |

OTHER PUBLICATIONS

Bolton et al., "Labelling of Proteins", Biochem. J. (1973), 133, 529–539.

Lancone John J., "Radioioponation", Methods in Enzymology, vol. 70, 1980, 221–235.

Wilbur et al., "Radiohalogenation", J. Lab. Comps. & Pahrms. vol. XIX, No. 10, 1982 1171–1188.

Z. V. Svitra et al, "Synthesis and Reactions of p–Trimethylsilylphenyl–propionic Acid", Seventh Rocky Mountain Regional ACS Meetings, Albuquerque, New Mexico, Jun. 6–8, 1984.

D. S. Wilbur et al., "Radiolabeled Phenylalkanoic Acids for Protein Labeling. Investigation of Arylsilanes as Intermediates for Radiolabeled Phenylpropionic Acids and Acid Derivatives", International Chemical Congress of Pacific Basin Societies, Honolulu, Hawaii, Dec 16–21, 1984.

Blau et al., "p–Iodobenzoyl Groups as a Paired Label for in vitro Protein Distribution Studies: Specific Localization of Anti–tissue Antibodies," *International Journal of Applied Radiation and Isotopes* 3:217–225, 1958.

Wilbur and Svitra, "Electrophilic Radiobrominations of Hippuric Acid: An Exampleof the Utility of Aryltrime- (List continued on next page.)

*Primary Examiner*—John S. Maples
*Attorney, Agent, or Firm*—Debra K. Leith

[57] ABSTRACT

Haloaryl compounds bearing a defined functional group or precursor are metalated with either SN(n-Bu)$_3$ or SnMe$_3$. The resulting aryltin compound may be transmetalated in site-specific reaction with one of the following organometallic groups: HgX$_2$, Hg(OAc)$_2$, BX$_3$, or BZ$_3$, wherein X is Cl, Br, or I, and Z is alkyl or alkoxy. The stannylated or otherwise metalated compounds are subsequently radiohalogenated via a demetalation reaction. The Stannylated or otherwise metalated compounds are subsequently radiohalogenated via a demetalation reaction. The functional group is suitable for conjugation to protein and can be present or be added subsequent, but most preferably prior, to the radiohalogenation.

Also compounds of the formula: R$_1$—Ar—R$_2$, wherein R$_1$ is either a radiohalogen or any one of the organometallic groups stated above, Ar is aromatic or heteroaromatic ring, and R$_2$ is a short-chain substituent that does not highly activate the aromatic ring an that bears a functional group suitable for conjugation to protein under conditions that preserve the biological activity of the protein. The radiohalogenated small nolecules are conjugated to proteins such as monoclonal antibodies for use in diagnosis and therapy.

24 Claims, 4 Drawing Sheets

OTHER PUBLICATIONS thylsilane Intermediates", *Journal of Labelled Compounds and Radiopharmaceuticals* vol. XXI, No. 5, pp. 415–428, 1984.

Riley and Perham, "The Reaction of Protein Amino Groups with Methyl5–Iodopyridine–2–carboximidate", *Biochem. J.* 131:625–635, 1973.

Coleman et al., "Aromatic Radiobromination Without Added Carrier", *J. Chem. Soc., Chem. Comun.* 1982, pp. 1276–1277.

Visser et al., "The Preparation of Aromatic Astatine Compounds Through Aromatic Mercury-Compounds", *Journal of Labelled Compounds and Radiopharmaceuticals,* vol. XVIII, No. 5, pp. 657–665, 1980.

Gilliland et al., "Iodine Labelled Radiopharmaceuticals from Arylthallium Bis(trifluoroacetate) Intermediates, "*Journal of Radioanalytical Chemistry* 65:107–113, 1981.

M. Kosugi et al., "Palladium Catalyzed Reaction of Hexabutylditin with Aryl Bromides: Preparation of Negatively Substituted Aryltributyltin", *Chemistry Letters,* pp. 829–830, The Chemical Society of Japan, 1981.

Parham and Jones, "Elaboration of Bromoarylinitriles", *J. Org. Chem.* 41: 1187–1191, 1976.

Wursthorn and Kuivila, "Synthesis of Substituted Aryltrimethylstannanes by the Reaction of Trimethylstannylsodium with Aryl Bromides", *Journal of Organometallic Chemistry* 140: 29–39, 1977.

RADIOHALOGENATED PROTEINS

This application is a continuation application based on prior copending application Ser. No. 852,740, filed on Apr. 21, 1986 now abandoned.

This application is a continuation-in-part of applicants' copending application Ser. No. 735,392, filed May 17, 1985, now abandoned.

TECHNICAL FIELD

This invention relates to radiohalogenated small molecules for labeling proteins, particularly antibodies, useful for clinical diagnosis and therapy, and to methods of introducing high specific activity radiohalogens into protein molecules.

BACKGROUND OF THE INVENTION

Radiohalogenated proteins have been the object of extensive scientific study and promise to be useful for a variety of clinical applications, both in vitro and in vivo. For example, radioiodinated ferritin is used in an in vitro diagnostic determination of ferritin concentration in serum. Radioiodinated thyroid stimulting hormone is employed in a similar assay.

Radionuclides of halogens possess properties that make them very attractive for both diagnostic imaging and radiotherapy. For example, radioiodine as iodine-123 ($T\frac{1}{2}$=13 h, 159 keV gamma, electron capture) is nearly ideal for imaging with the current gamma cameras, and iodine-131 ($T\frac{1}{2}$=8 d, 364 keV gamma, beta particle), while producing images of lower quality, has been demonstrated to be useful in clinical radiotherapy of the thyroid. Similarly, bromine radionuclides such as bromine-75 ($T\frac{1}{2}$=1.6 h, positron) and bromine-76 ($T\frac{1}{2}$=16 h, positron) have properties that make them attractive for positron tomographic imaging, and bromine-77 ($T\frac{1}{2}$=2.4 d, several gammas, electron capture) has properties that make it attractive for radiotherapy. Other radiohalogens, such as fluorine-18 ($T\frac{1}{2}$=110 min, positron) and astatine-211 ($T\frac{1}{2}$=7.2 h, alpha particle), are also attractive candidates for radioimaging and radiotherapy.

The development of monoclonal antibodies which localize in cancerous tissue due to their high specificity and affinity for antigens on tumor cell surfaces has increased the prospect of clinical applications of radiolabeled antibodies for diagnosis and/or therapy. The high specificity of the antibodies make them desirable candidates as carrier molecules to attach specific radionuclides for delivering radioactivity to a cancer site.

Unfortunately, there are presently no routine clinical diagnostic or therapeutic applications of radiohalogen labeled antibodies for use in vivo. Direct radiohalogen labeling of antibodies and other proteins has proved to be difficult. Antibodies exhibit varying sensitivities to radiolabeling reaction conditions, and the oxidizing reaction conditions necessary for radiohalogenations are particularly deleterious. Direct radioiodination of proteins has become routine, but very often a measurable reduction of biological activity of the protein results. The stability of the attached radiolabel can also vary. For example, the loss of radioiodine from antibodies has been found to be as high as 50% in 24 hours for some labeled antibodies. Radiobrominations require even stronger oxidizing reaction conditions than radioiodinations, and attempts to radiobrominate proteins directly have met with little success unless expensive and difficult to obtain enzymes are used as oxidants. Furthermore, direct radiohalogenation of proteins occurs primarily at tyrosyl rasidues, and the activated phenol ring of tyrosine contributes to an inherent electronic instability of the resultant ortho-substituted radiohalogen label. The radiohalogen label is also subject to steric hindrance effects and may in addition be available to deiodinase enzymes which catabolize the structurally similar thyroid hormones, e.g., thyroxine.

One approach that circumvents subjecting proteins to the harsh reaction conditions necessary for direct radiohalogenations is the use of small molecules that can be radiolabeled in a separate reaction vessel and subsequently coupled to proteins under mild reaction conditions. This approach is the basis of the commercially available Bolton-Hunter reagent, N-succinimidyl-3-(4-hydroxyphenyl)propionate. Moderate radiolabeling yields are thereby obtained with radioiodine (35–60% yields of labeled proteins), but the stability of the radioiodine label suffers from the same problems as described for the chemically similar radioiodinated tyrosyl residues. Similarly, the commercially available Wood's reagent, methyl-4-hydroxybenzimidate, can be radioiodinated prior to attachment to proteins. However, the radioiodinated product is also plagued with the inherent instability of the ortho-iodinated phenol. Even though these reagents do not yield as stable a radiolabel as desirable, they have been extensively used for radioiodination because little deactivation of the protein results from their use.

The phenolic ring is employed in both the Bolton-Hunter and Wood's reagents because an activated aromatic ring is required in order to introduce high specific activity radioiodine into these molecules. It would be very desirable to be able to introduce radiohalogens into small molecules containing an aromatic ring other than a phenol so that the radiolabel would be more stably attached; furthermore, if the hydroxyl were not present the radiolabel would be less subject to electronic and steric hindrance effects.

Recent reports in the literature describe the use of organometallic intermediates to introduce high specific activity radiohalogens into non-activated aromatic rings of simple organic molecules, but not into more complex organic molecules that can be attached to proteins without the aforementioned disadvantages.

SUMMARY OF THE INVENTION

This invention provides a rapid and efficient method of introducing high specific activity halogen radionuclides into non-activated aromatic rings of small molecules that can be conjugated to proteins under conditions that preserve the biological activity of the protein. Substitution of the radiohalogen onto a non-activated aromatic ring provides a radiolabeled protein with greater stability than prior art substitutions onto activated aromatic rings such as phenols. Furthermore, the radiohalogen can be substituted in positions such as para or meta on an aromatic ring which does not contain a hydroxy functionality in order to render the radiolabel less susceptible to attack by deiodinase enzymes.

Pursuant to this method, haloaryl compounds are metalated with one of the following organometallic groups: Sn(n-Bu)$_3$ or SnMe$_3$. The resulting aryltin compound can be transmetalated in a site-specific reaction with one of the following organometallic groups: HgX$_2$, Hg(OAc)$_2$, BX$_3$, or BZ$_3$, wherein X is Cl, Br, or I, and Z is alkyl or alkoxy. The metalated compounds are subsequently radiohalogenated via a demetalation reaction. A functional group suitable for conjugation to protein can be added subsequently or preferably prior to the radiohalogenation.

Also provided are compounds of the formula: $R_1$—Ar—$R_2$, wherein $R_1$ is either a radiohalogen or any one of the organometallic groups stated above, Ar is aromatic or heteraromatic ring, and $R_2$ is a short-chain substituent that does not highly activate the aromatic ring and that bears a functional group suitable for conjugation to protein under conditions that preserve the biological activity of the protein. The radiohalogenated small molecules of this invention can be conjugated to proteins such as monoclonal antibodies for use in diagnosis and therapy.

DESCRIPTION OF THE PREFERRED EMBODIMENT

Figure 1:
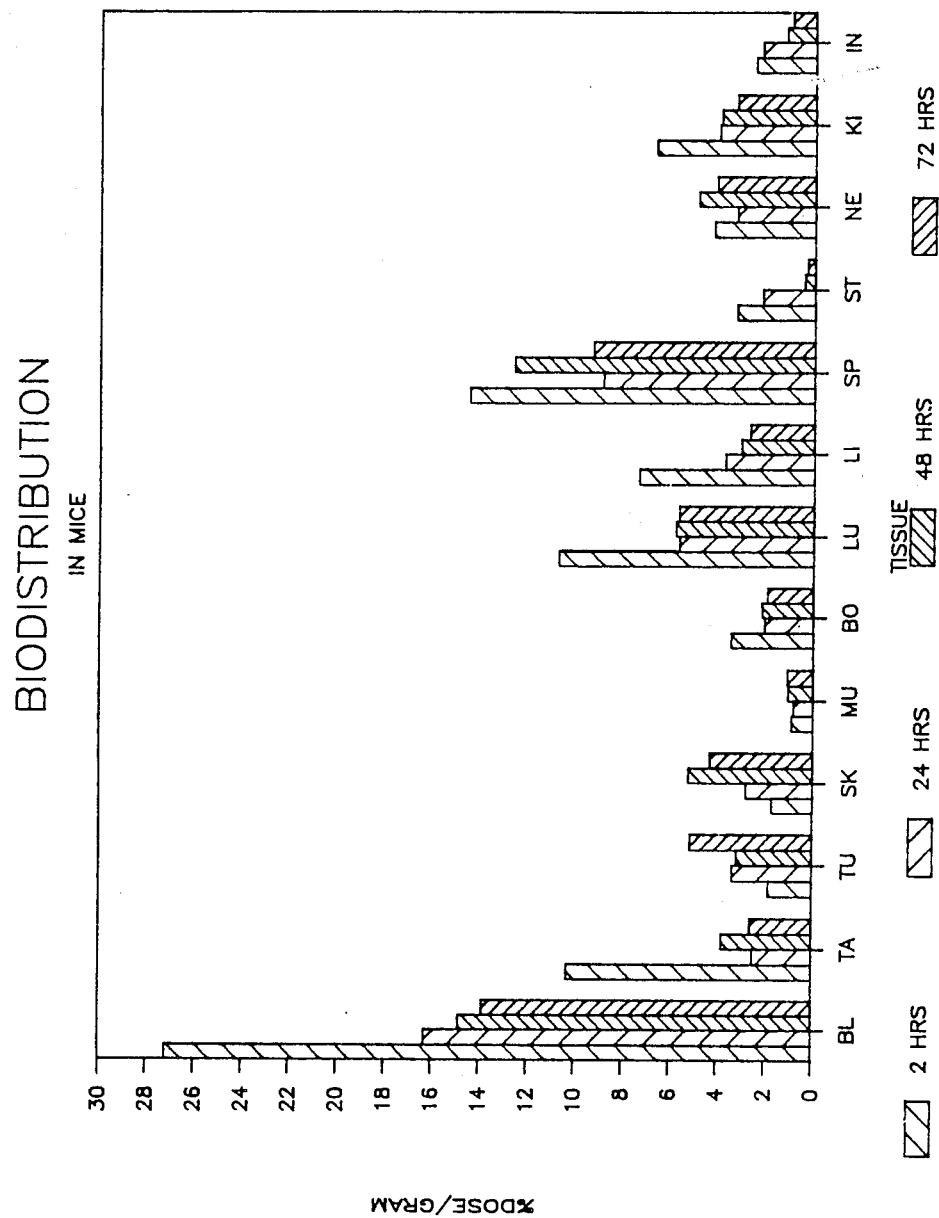
FIGS. 1, 2, 3 and 4 are bar graphs presenting comparative biodistribution data that confirms, as described in Example 14, the enhanced in vivo stability of monoclonal antibodies radiolabeled pursuant to this disclosure.

The present invention is directed to radiohalogenated small molecules of the formula ):

    I wherein
*X is a radiohalogen,
Ar is aromatic or heteroaromatic ring, and
R is a short-chain substituent that does not highly activate ring Ar onto which radiohalogen *X is substituted and that bears a functional group suitable for conjugation to protein under mild, e.g., acylation, conditions that preserve the biological activity of the protein. The compounds of formula I can be coupled to proteins, such as monoclonal antibodies or plasma proteins (or to carriers such as amino acid polymers which can in turn be coupled to proteins), to provide reagents for diagnostic and therapeutic applications.

As utilized herein, the symbol *X indicates any radioisotope of: iodine, particularly I-123, I-15, and I-131; bromine, particularly Br-75, Br-76, and Br-77; fluorine, particularly F-18; and, astatine, particularly At-211. Preferred radiohalogens *X for diagnostic imaging purposes include I-131 and most preferably I-123 for imaging with gamma cameras; and for positron tomographic imaging: R-18, Br-75, and Br-76. For clinical radiotherapy, preferred radiohalogens *X include I-131, Br-77, and At-211. Preferred radiohalogens *X for in vitro radioimmunoassay purposes include I-125 and I-131. Pursuant to this invention the radiohalogen *X is preferably para- or metal-positioned on ring Ar relative to substituent R in order to render the radiohalogen less susceptable to catabolism by dehalogenase enzymes.

The symbol Ar indicates any aromatic or heteroaromatic ring. Preferred rings Ar include benzene, pyridine, furan, the thiophene, the latter three because of the enhanced water solubility they convey. The attachment of the radiohalogen to a carbon atom in ring Ar is preferred over attachment to an alkyl carbon atom due to the increased bond strength of the carbon-halogen bond in the aromatic or heteroaromatic ring. The nature of the ring Ar is not critical and may be mono-, bi-, tri-, or higher number of rings, but a monocyclic ring is preferred because of increased water solubility. Ring Ar may consist of all carbon atoms or may contain heteroatoms such as nitrogen oxygen, or sulfur. Inclusion of heteroaromatic rings such as pyridines, furans, or thiophenes can assist in increasing the water solubility of the radioiodinated small molecule conjugates. Further substitution on the ring Ar, exclusive of *X and R, with polar substituents such as a nitro, sulfonic acid, carboxylic acid, or dialkyl amino group can also be used to enhance water solubility. Increased water solubility is desirable to give higher yields (and less potential aggregation) in the conjugation reaction with protein, and to cause less perturbation of the lipophilicity of the antibody conjugate. Other substituents can be added to impart some control against enzymatic degradation.

The symbol R indicates any substituent that meets the following three requirements: First, the R substituent must not highly activate ring Ar toward electrophilic substitution. In other words, R cannot be linked to ring Ar by a linkage that increases the electron density of Ar on the order of the increase produced by a free hydroxy or primary amino substitution. Second, R should be a short-chain substituent so that unconjugated or cleaved radiohalogenated molecules can be rapidly removed by the kidneys. Thus, R may contain an alkyl or other spacer chain between the aryl linkage and the functional group for protein conjugation, but such a spacer chain should preferably contain no than 5, and most preferably no more than 3, straightchain carbon atoms. Third, the R substituent should bear a functional group that is available for conjugation to protein under mild conjugation conditions, such as acylation or amidination, that preserve the biological activity of the protein. Thus, R should provide a functional group (termed Q herein), such as imide ester or imidate ester, for covalent attachment to corresponding functional groups (or conjugated attachment sites) on amino acid or carbohydrate residues of proteins, glycoproteins, or carrier molecules such as amino acid polymers that can in turn be conjugated to protein molecules.

Suitable functional groups Q for the above-stated purpose include phenolic esters (e.g., para-nitrophenol), imide esters (e.g., succinimide ester), imidate esters, anhydrides, acylsuccinimides, aldehydes, isothiocyanates, thiol, diazo, amines, hydrazines, alkyl halides, Michael acceptor $\alpha,\beta$-unsaturated carbonyl compounds such as maleimides, and other groups that can be used to attach the molecule to a protein through a covalent bond. Also provided are radiohalogenated small molecules of formula I wherein the R substituent bears a precursor of functional group Q. Suitable precursors include: carboxylic acid where Q is phenolic ester, imide ester, anhydride, acylsuccinimide, or maleimide; nitrile where Q is imidate ester; alcohol where Q is aldehyde; halide where Q is isothiocyanate, thiol, hydrazine, or amine; and amine where Q is diazo or maleimide.

Representative R substituents include imide ester, alkyl imide esters, amido alkyl imide esters, imidate ester, alkyl imidate esters, and amido alkyl imidate esters.

Representative radiohalogenated small molecules of this invention include the compounds of formulas II and III:

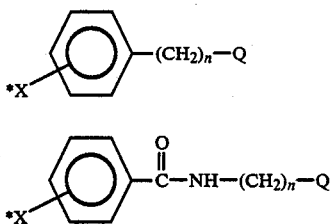

wherein
*X is radiohalogen as stated above,
n is an integer, and
Q is a functional group as stated above.

The radiohalogen may be positioned as any regioisomer on the aromatic ring Ar, but para- or meta-substitution is preferred in order to make the radiohalogen less susceptible to steric instability and catabolism by deiodinase enzymes. The spacer component $(CH_2)_n$ can be a straight- or branched-chain alkyl or heteroalkyl group containing up to 12 but preferably no more than 5 straight-chain carbon atoms. In the most preferred embodiments no more than three straight-chain carbon atoms separate functional group Q from the aromatic ring; i.e., n=0, 1, 2, or 3. In order to quickly clear background activity for diagnostic imaging, and to minimize radiation does to vital organs, the alkyl spacer component should be shortened so that nonconjugated and chemically or enzymatically cleaved radiohalogenated compounds can be rapidly cleared through the kidneys, rather than via fatty acid degradation pathways in the heart or liver. On the other hand, for certain applications a short alkyl or heteroalkyl spacer between the radiolabeled aryl ring and the protein may be desirable.

Illustrative but nonlimiting examples of radiohalogenated small molecules of this invention include: N-succinimidyl 3-(4'-[$^{131}$I]iodophenyl)propionate; methyl 3-(4'-[$^{131}$I]iodophenyl)propionimidate; N-succinimidyl 4-[$^{131}$I]iodobenzoate; methyl 4-[$^{131}$I]iodobenzimidate; N-succinimidyl 4-[$^{131}$I]iodobenzamidoacetate or N-succinimidyl 4-[$^{131}$I]iodohippurate; methyl 4-[$^{131}$I]iodobenzamidoacetimidate; and 4-[$^{131}$I]iodobenzamidoacetonitrile.

Also provided by the present invention are organometallic intermediate molecules of formula IV:

M—Ar—R     IV wherein M is Sn(n-Bu)$_3$, (Bu being butyl), SnMe$_3$, (Me being methyl), HgX, (X being Cl, Br, or I), HgOAc, (OAc being acetate), B(OH)$_2$, or BZ$_2$, (Z being alkyl or alkoxy containing no more than five, and preferably fewer, carbon atoms), with both Ar and R as defined with reference to Formula I. Organometallic group M is preferably para- or meta-positioned. Illustrative but nonlimiting examples of organometallic intermediate molecules of this invention include: N-succinimidyl 3-(4'-tributylstannylphenyl)propionate; methyl 3-(4'-tributylstannylphenyl)propioimidate; N-succinimidyl 4-tributylstannylbenzoate; methyl 4-tributylstannylbenzimidate; N-succinimidyl 4-tributylstannylbenzamidoacetate or N-succinimidyl 4-tributylstannylhippurate; methyl 4-tributylstannylbenzamidoacetimidate; and 4-tributylstannylbenzamidoacetonitrile.

A method is provided for synthesizing the compounds of formula I. Briefly stated, one of three reactions described below may be used to metalate any positioned isomer of a haloaromatic derivative bearing a functional group Q or a precursor to a functional group Q. The metalation will employ a trialkyltin reagent such as Sn(n-Bu)$_3$ or SnMe$_3$. The resulting aryltin compound can be transmetalated in site-specific reaction with one of the following organomercury or organoboron reagents: HgX$_2$, Hg(OAc)$_2$, BX$_3$, or BZ$_3$, wherein X is Br, I, or preferably Cl, and Z is alkyl or alkoxy. The resulting organometallic intermediates can alternatively be made via metalation reactions as referenced below. The stannylated or otherwise metalated compound is radiohalogenated via a demetalation reaction, preferably after functional group Q is present.

The stated organometallic reagents are available through known chemistry and are commercially available, e.g., from Alpha Products, Danvers, MA.

Precursors of the organometallic intermediate molecules of formula IV are available through known chemistry or are commercially available. Suitable precursor molecules include: para-bromo and para-iodobenzoic acids (Pfaltz and Bauer, Stamford, Conn.); para-bromo and para-iodobenzonitriles (Pfaltz and Bauer). Synthesis of para-bromophenylpropionic acid in high yield is described below in Example 1. Conversion of the acid to the corresponding nitrile can be accomplished as described in *J. Org. Chem.* 41(7): 1187–1191, 1976.

Syntheses of the arylstannanes can be carried out via any one of the following three distinctly different reactions. In the first reaction, the haloaromatic compound is reacted with n-butyl lithium at near $-100°$ C. or with magnesium at room temperature, followed by reaction of the aryl metal with a halide derivative of a trialkyltin reagent, preferably tri-n-butyltin. In the second reaction, the haloaromatic compound is reacted with hexaalkylditin and tetrakis(triphenylphosphine)palladium. In the third reaction, the haloaromatic compound is reacted with a trialkylstannyl alkali (e.g., trimethylstannyl sodium) in tetraglyme at 0° C.

Syntheses of organomercurial and organoboron intermediates can be carried out by previously described methods (*Organometallic Chem. Rev.* 1: 305–329, 1966; *Tetrahedron* 38(12): 1713–1754, 1982) or preferably by transmetalation of the above arylstannanes. Transmetalation of an aryltin compound with one of the stated organomercury or organoboron groups can be made to achieve a site-specific substitution onto the aromatic ring. For example, transmetalation with BCl$_3$ yields the corresponding aryl-BCl$_2$ compound, which can then be base converted to the corresponding aryl-B(OH)$_2$ compound. Reaction with Hg(OAc)$_2$ yields the corresponding aryl-HgOAc compound which can be further converted to aryl-HgX by reaction with halide ion (X).

Attaching the yet-to-be radiolabeled compounds to proteins will require the availability of a functional group Q, such as can be provided by conversion of a carboxylate precursor group into an ester containing a good leaving group, for example hydroxysuccinimide, or by conversion of a cyano precursor into an imidate ester. Such conversions can be considered as activating the molecule towards reaction with a corresponding functional group, such as an amino group (e.g., lysine residues), a thiol or hydroxy, (or, less preferably, a carboxylate), on a protein. Due to the nucleophilic nature of the alkali metal intermediates, when these reagents are used the activated imide and imidate esters or other nucleophilic reagent sensitive above-stated functional groups Q can only be synthesized after introducing the trialkyltin functionality onto the aromatic ring. Therefore, we have found that the second arylstannane synthesis reaction is particularly useful for preparing compounds that are sensitive to nucleophilic reactions. Making the activated imide and imidate esters or other functional group Q prior to introducing the radiohalogen avoids losses in radiochemical yields and the incorporation of radiochemical impurities that would otherwise result.

Conversion of the aryltin or otherwise melatated derivatives from free carboxylic acids or their stannyl esters to N-succinimidyl esters can be accomplished prior to the radiohalogenation step, using dicyclohexylcarbodiimide (DCC) and N-hydroxysuccinimide (NHS) in anhydrous tetrahydrofuran (THF). However, synthesis of imidate esters from cyano compounds is made problematical by the acid instability of the aryl-metal bond, particularly the aryltin bond. Thus, cyano containing compounds may be radiohalogenated prior to formation of the imidate ester. The preferred method is to form the imidate ester of the corresponding halobenzonitrile or haloarylalkyl nitrile, and subsequently metalate the imidate containing compound using hexaalkylditin and tetrakis(triphenylphosphine)palladium (using the second arylstannane synthesis route).

Radiohalogenation of the corresponding N-succinimidyl esters will yield the desired compounds via a site-specific demetalation reaction. Due to the possibility of hydrolysis of the N-succinimidyl esters, the reactions should be carried out using conditions that will minimize the reaction time. For example, the reactants can be brought to room temperature in order to minimize the hydrolysis by shortening the reaction time. Alternatively, reaction mixtures in which the hydrolysis is relatively slow can be used. Surprisingly, addition of acetic acid to the reaction mixture significantly slows the N-succinimidyl ester hydrolysis. For example, the N-succinimidyl ester of 4-tri-n-butylstannylbenzoate has been found to be stable for months in 5% acetic acid/methanol solution, advantageously eliminating the short time constraints routinely encountered with, e.g., the Bolton-Hunter method.

The radiohalogenation reaction mixture should have a dilute sodium thiosulfate solution added to it prior to any purification or workup procedure. Separation of any remaining radiohalide can then be easily accomplished prior to or during purification of the radiolabeled protein via chromatographic separations.

The radiohalogenation reactions are preferably carried out in protic solvents such as water, methanol, ethanol, or mixtures thereof. The alcoholic solvents can be conveniently removed prior to addition of the radioactive compound to the protein solution (or vice versa). Alternatively, nonprotic solvents (e.g., carbon tetrachloride) can be used for radiohalogenation since a biphasic system may provide a convenient method of separating free radiohalide from the labeled compounds.

The radiohalogenations can be monitored and purified by radio-HPLC, for example on a reverse-phase high performance liquid chromatography column (C-18) eluted with a mixture of MeOH/1% HOAc in $H_2O$.

Also provided are radiopharmaceutical kits for clinical use which include a vial containing a compound (IV) that has an appropriate functional group Q along with the appropriate reagents such that introduction of a radiohalogen will give the desired radiohalogenated molecule. The radiohalogenated product can then be conjugated to protein, such as a monoclonal antibody supplied in a separate vial. The kit may also include one or more small columns for chromatographic separation of remaining precursors and impurities from the radiohalogenated protein product.

This invention is further illustrated by the following Examples.

EXAMPLE 1

Synthesis of 3-(4'-bromophenyl)propionic acid

A flask containing 10.0 g 2,4,4-trimethyl-2-oxazoline (88 mmol) dissolved in anhydrous tetrahydrofuran (THF) under nitrogen was allowed to equilibrate at $-78°$ C. (dry ice/acetone bath) for 10 minutes. To this flask was slowly added 55 mL of n-butyl lithium (1.6N, 85 mmol). The light yellow solution was then transferred to a second flask containing 29.4 g (100 mmol) 4-bromobenzylbromide in 200 mL anhydrous THF under nitrogen at $-78°$ C. Once the addition was complete, the reaction mixture was stirred for 20 minutes at $-78°$ C.; then the cooling bath was removed and the stirring was continued for 3 hours.

A 200 mL volume of saturated $NH_4Cl$ was added (cautiously) and the two phases were separated. The THF layer was dried over anhydrous $MgSO_4$ and evaporated to yield an oil. This oil was dissooved in 200 mL dimethoxyethane and 100 mL 3N HCl, and was heated to reflux for 5 hours. The resultant solution was poured onto ice, and the light tan solid was collected (yield: 17 g).

This solid was dissolved in approximately 300 mL 15% KOH and extracted with 200 mL diethyl ether. The KOH solution was diluted with ice and acidified with concentrated HCl. The white precipitate was collected and washed well with $H_2O$ (yield: 10 g).

EXAMPLE 2

Synthesis of 4-tri-n-butylstannylbenzonitrile

A flask containing 1 equivalent (e.g., 10 mmol) of 4-bromobenzonitrile in freshly distilled anhydrous THF was allowed to equilibrate at approximately $-100°$ C. (diethyl ether/liquid nitrogen bath) for approximately 30 minutes under nitrogen. To the flask was then added 1.1 equivalents (e.g., 11 mmol) of a n-butyl lithium solution (2.3M in hexanes) at such a rate as to keep the reaction temperature below $-90°$ C. After the addition was completed, the reaction mixture was stirred at approximately $-100°$ C. for an additional five minutes.

Then a solution of 1.1 equivalents (e.g., 11 mmol) of tri-n-butyltin chloride in anhydrous THF was added dropwise. As before, the addition was made at such a rate as to keep the reaction temperature below $-90°$ C. After the addition was completed, the reaction mixture was stirred at $-100°$ C. for 30 minutes. The cooling bath was then removed and the reaction mixture was allowed to come to room temperature over a two hour period.

The THF was then removed by rotary evaporation to yield a milky oil. This oil was dissolved in $CH_2Cl_2$, washed with $H_2O$, and dried over $MgSO_4$. Evaporation of the $CH_2Cl_2$ yielded (96%) a faint yellow oil. Purification of this oil by distillation at 132° C./100 microns gave a colorless oil which was 85% pure by HPLC analysis: $^1H$ NMR $(CDCl_3)\delta$ 0.68–2.0 (m, 27H), 7.68 (s, 4H).

EXAMPLE 3

Syntheses of tri-n-butylstannyl 4-(tri-n-butylstannyl)benzoate

Method 1: To a solution of 2.01 g (10 mmol) of 4-bromobenzoic acid (Alfa Products) in 100 mL of anhydrous THF cooled to −100° C. (diethyl ether/liquid nitrogen) (in a flask equipped with thermometer, addition funnel, and magnetic stirring bar) was added dropwise 13.5 mL (21 mmol) of 1.55N n-butyl lithium in hexane (Aldrich) at such a rate that the internal temperature did not exceed −90° C. The viscous mixture was allowed to warm to −78° C., and 5.70 mL (6.83 g, 21 mmol) of n-tributyltin chloride (Alrich) was added over 15 minutes. When addition was completed, the mixture was allowed to come to room temperature and stirred for 1 hour. To the mixture was then added 150 mL of saturated $(NH_4)_2SO_4$ solution, and the mixture was extracted with 150 mL of diethyl ether. The upper layer was washed with brine, dried ($MgSO_4$), filtered, and concentrated to give 7.49 g of liquid. Purification by silica gel chromatography (25% EtOAc/hexane) gave 2.32 g (33%) of tri-n-butylstannyl 4-(tri-n-butylstannyl)benzoate as a viscous oil: $^1$H NMR ($CCl_4$)δ 0.32–2.70 (m, 54H), 7.50 (d, J=7 Hz, 2H), 7.99 (d, J=7 Hz, 2H). IR (neat) 1635, 1450, 1315 cm$^{-1}$.

Method 2: To a stirred suspension of 1.00 g (5 mmol) of 4-bromobenzoic acid (Alpha) in 7.6 mL of hexabutylditin (Alfa) and 10 mL of toluene under $N_2$ atmosphere was added 58 mg of tetrakis(triphenylphosphine)palladium(O) (Aldrich), and the mixture was stirred at 95° C. for 20 hours. When cool, the orange mixture was partitioned between 100 mL of 10% aqueous KF solution and 100 mL of diethyl ether. The ether layer was washed with brine, dried ($MgSO_4$), filtered, concentrated, and distilled by Kugelrohr to yield 1.14 g (33%) of tri-n-butylstannyl 4-(tri-n-butylstannyl)benzoate as a viscous oil: distilled at 200°–250° C., 0.25 mmHg.

EXAMPLE 4

Synthesis of N-succinimidyl 4-(tri-n-butylstannyl)benzoate

To a solution of 1.29 g (1.84 mmol) of tri-n-butylstannyl 4-(tri-n-butylstannyl)benzoate in 18.4 mL of anhydrous THF was added 417 mg (2.02 mmol) of dicyclohexylcarbodiimide (Sigma) and 212 mg (1.84 mmol) of N-hydroxysuccinimide (Sigma, and the mixture was stirred for 15 hours at room temperature. To the mixture was then added three drops of HOAc. The solids were removed by filtration, and the mixture was concentrated. Purification by silica gel chromatography (25% EtOAc/hexane) yielded 731 mg (78%) of N-succinimidyl 4-(tri-n-butylstannyl)benzoate: $^1$H NMR ($CDCl_3$)δ 0.50–2.20 (m, 27H), 2.90 (s, 4H), 7.65 (d, J=8 Hz, 2H), 8.06 (d, J=8 Hz, 2H). IR (neat) 1780, 1750, 1190, 1055, 980 cm$^{-1}$.

EXAMPLE 5

Synthesis of 4-(tri-n-butylstannyl)hippuric acid

To a solution of 406 mg (0.80 mmol) of N-succinimidyl 4-(tri-n-butylstannyl)benzoate in 6.4 mL of $CH_3CN$ was added 224 μL (160 mg, 1.60 mmol) of $Et_3N$ (Fisher) followed by a solution of 60 mg (0.80 mmol) of glycine (Fisher) in 1.6 mL of $H_2O$. The mixture was stirred for 1 hour at room temperature and then partitioned between 10 mL of 5% aqueous HCl solution and 10 mL of $Et_2O$. The $Et_2O$ layer was washed with brine, dried ($MgSO_4$), filtered, and concentrated to give 374 mg (100%) of 4-(tri-n-butylstannyl)hippuric acid, a viscous oil pure enough for further reaction: $^1$H NMR ($CDCl_3$)δ 0.40–2.50 (m, 27H), 3.94–4.53 (m, 2H), 6.70–7.25 (m, 1H), 7.53 (d, J=8 Hz, 2H), 7.80 (d, J=8 Hz, 2H), 9.00–9.65 (brd s, 1H). IR (neat) 3600–2300 broad with more intense absorbance at 3330, 1720, 1635, 1535 cm$^{-1}$.

EXAMPLE 6

Synthesis of N-succinimidyl 4-(tri-n-butylstannyl)hippurate

To a solution of 378 mg (0.80 mmol) of 4-(tri-n-butylstannyl)hippuric acid in 8 mL of THF was added 182 mg of dicyclohexylcarbodiimide (Sigma) followed by 92 mg of N-hydroxysuccinimide (Sigma). The mixture was stirred at room temperature for 6 hours, and 3 drops of acetic acid were then added. The mixture was filtered, and the filtrate was concentrated to an oily solid. Purification by chromatography on silica gel (50% EtOAc/hexane) gave pure N-succinimidyl 4-(tri-n-butylstannyl)hippurate 158 mg (35%) as a white solid: mp 109°–111° C. (EtOAc/hexane); $^1$H NMR ($CDCl_3$)δ 0.33–2.27 (m, 27H), 2.85 (s, 4H), 4.66 (d, J=6 Hz, 2H), 7.02 (t, J=6 Hz, 1H), 7.63 (d, J=8 Hz, 2H), 7.89 (d, J=8 Hz, 2H).

EXAMPLE 7

Synthesis of tri-n-butylstannyl 3-(4'-tri-n-butylstannylphenyl)propionate

A solution of 2.29 g (10 mmol) of 3-(4'-bromophenyl)propionic acid in 125 mL of THF and 25 mL of hexane (in a flask fitted with $N_2$ inlet, addition funnel, and thermometer, under $N_2$ atmosphere) was cooled to =100° C. (diethyl ether/liquid nitrogen). To the solution was added dropwise 13.5 mL (21 mmol) of a 1.55M solution of butyl lithium in hexane (Aldrich) at such a rate that the temperature of the solution did not exceed −90° C. The resulting viscous mass was allowed to warm to −75° C. over ½ hour, and 5.70 mL of n-tributyltin chloride (Aldrich) was added dropwise over 1 minute. The mixture then again became fluid and was stirred at −75° C. for 30 minutes. The cooling bath was then removed, and the mixture was stirred until it reached room temperature. To the mixture was added 100 mL of saturated $(NH_4)_2SO_4$ solution. After shaking in a separatory funnel, the upper layer was washed successively with 100 mL of 10% KF solution and with 50 mL of brine, dried with $MgSO_4$, filtered, and concentratred to give 7.5 g of waxy solid. Two recrystallizations of 1.00 g. of this material from $H_2O$/acetone yielded 405 mg (42%) of tri-n-butylstannyl 3-(4'-tri-n-butylstannylphenyl)propionate as a white powder: mp 59°–60° C.; $^1$H NMR ($CDCl_3$)δS 0.50–2.34 (m, 54H), 2.75 (m, 4H), 7.23 (d, J=8 Hz, 2H), 7.45 (d, J=8 Hz, 2H); IR (melt) 1695, 1530 cm$^{-1}$.

EXAMPLE 8

Synthesis of N-succinimidyl 3-(4'-tri-n-butylstannylphenyl)propionate

To a solution of 460 mg (0.63 mmol) of tri-n-butylstannyl 3-(4'-tri-n-butylstannylphenyl)propionate in 6.5 mL of anhydrous THF was added 143 mg (0.69 mmol) of dicyclohexylcarbodiimide (Sigma) followed by 73 mg (0.63 mmol) of N-hydroxysuccinimide (Sigma). The mixture was stirred for 24 hours, and 37 μL (38 mg, 0.63 mmol) of acetic acid was added. The mixture was filtered and concentrated. Purification by silica gel chromatography (30% EtOAc/hexane) yielded on the order of 195 mg (58%) of N-succinimidyl 3-(4'-tri-n-butylstannylphenyl)propionate as a viscous oil: $^1$H NMR (CDCl$_3$)δ 0.38–2.15 (m, 27H), 2.53–3.32 (m, 8H), 7.20 (d, J=8 Hz, 2H), 7.38 (d, J=8 Hz, 2H); IR (neat) 1820, 1790, 1740, 1185, 1045 cm$^{-1}$.

EXAMPLE 9

Synthesis of methyl 4-bromobenzimidate

HCl gas was bubbled through a suspension of 7.2 g (40 mmol) of 4-bromobenzonitrile (Pfaltz and Bauer) in 20 mL of methanol until all the solid went into solution. The mixture was placed in a refrigerator at 4° C. for 90 hours, by which time long needles of the hydrochloride salt of methyl 4-bromobenzimidate had formed. The salt was collected by vacuum filtration to give 8.17 g (81%) of long white needles, and converted to the base by partitioning 1.33 g of the HCl salt between 50 mL of ice cold 10% Na$_2$CO$_3$ solution and 50 mL of diethyl ether. The diethyl ether layer was washed with 50 mL of brine, dried with MgSO$_4$, filtered, concentrated, and recrystallized from hexane to give 0.83 g (60% overall yield) of pure methyl 4-bromobenzimidate as needles: mp 64°–65°; $^1$H NMR (CDCl$_3$)δ 3.91 (s, 3H), 7.60 (s, 4H), 7.53–7.90 (brd, 1H).

EXAMPLE 10

Synthesis of methyl 4-(tri-n-butylstannyl)benzimidate

To a solution of 214 mg (1.0 mmol) of methyl 4-bromobenzimidate in 2 mL of toluene under N$_2$ atmosphere was added 1.52 mL (1.74 g, 3.0 mmol) of hexabutylditin (Alfa) followed by 11 mg (0.01 mmol) of tetrakis(triphenylphosphine)palladium (0) (Aldrich). The mixture was heated at 75°–80° C. in an oil bath for 18 hours. When cool the mixture was partitioned between 10 mL of 10% aqueous KF solution and 10 mL of diethyl ether. The diethyl ether layer was dried with MgSO$_4$, filtered, and concentrated. Purification of the oily concentrate by silica gel chromatography (25% EtOAc/hexane) yielded 226 mg (53%) of pure methyl 4-(tri-n-butylstannyl)benzimidate as a viscous oil: $^1$H NMR (CCl$_4$)δ 0.54–2.18 (m, 27H), 3.87 (s, 3H), 7.45 (d, J=8 Hz, 2H), 7.67 (d, J=8 Hz, 2H); IR (neat) 3340, 1635 cm$^{-1}$.

EXAMPLE 11

Synthesis of 4-(3'-propionic acid)phenylmercuric bromide

To a solution of 96 mg (0.30 mmol) of mercuric acetate (Aldrich) in 15 mL of anhydrous THF at 20° C. (water bath) was added 1.72 mL of acetic acid followed by a solution of 218 mg of tri-n-butylstannyl 3-(4'-tri-n-butylstannylphenyl)propionate in 1 mL of THF. The resulting solution was stirred at 20° C. for 1 hour and 15 mL of aqueous 3% KBr solution was added. After another 1 hour, most of the THF was removed on the rotory evaporator until a white precipitate appeared and the mixture was diluted with 15 mL of H$_2$O. The precipitate was collected by vacuum filtration and washed with a small amount of EtOH to give 93 mg (72%) of 4-(3'-propionic acid)phenylmercuric bromide as a white solid: $^1$H NMR (DMSO-d$_6$)δ 2.23–3.09 (m, 4H), 7.15 (d, J=8 Hz, 2M), 7.39 (d, J=8 Hz, 2H); mass spectrum (CI) m/z 431,433 (M+18.7, 6.0), 351 (27), 133 (100).

Transmetalations involving organoboron groups are accomplished in like manner.

EXAMPLE 12

Rediodination of N-succinimidyl 4-(tributylstannyl)benzoate

To a vial containing 10–50 μg N-succinimidyl 4-(tri-n-butylstannyl)benzoate (0.02–0.10 μmol) in 50 μL of 5% HOAc/methanol was added 10–20 μg (0.08–0.15 μmol) N-chlorosuccinimide in 10–20 μL methanol. To this solution was added 10 μL Na$^{125}$I solution (diluted in Delbecco's phosphate buffered saline; Gibco Labs) (100 μCi-2 mCi). After 3–5 minutes, 20 μL of a 0.25 μg/mL solution of Na$_2$S$_2$O$_5$ was added. The reaction mixture was further diluted with 50 μL PBS solution, and a stream of N$_2$ was blown over the top of the solution until the volume was reduced to only aqueous (about 80 μL). Radiolabeling yields of 75°–95% were obtained. This material can be used directly for protein labeling experiments, as described below.

Radioiodination with iodine-131 was carried out in like manner with comparable yields.

EXAMPLE 13

Protein labeling with radiohalogenated small molecules

The above crude aqueous radioiodinated ester mixture was transferred to a vial containing buffered protein solution (pH 8.5–9), or vice versa. The conjugation reaction was complete with 5 minutes at room temperature. Conjugation yields ranged from about 35–60%. The labeled protein was purified from nonconjugated radioactivity using either a gel permeation chromatography column or a small pore filtration system (e.g., Centricon ultra centrifugation).

The radiohalogenated protein products of Example 13 can be used for radiodiagnosis and therapy. For example, monoclonal antibodies or antigen binding fragments that are specifically reactive with tumor cell associated antigens can be radiohalogenated by this method and then used for imaging tumor cell location in the body of a mammal: an appropriate amount of the radiohalogenated antibody can be introduced, e.g., by intravenous injection, into the patient's body, and thereafter the body can be scanned with a scintillation detector such as a gamma camera. Such radiohalogenated antibodies can also be introduced into the body of a mammal for the purpose of tumor radiotherapy.

Other proteins and peptides that tend to concentrate in an organ or diseased tissue can likewise be radiohalogenated by this method and used to monitor departures from homeostasis and disease states. For example, radiohalogenated fibrinogen can be used to localize deep vein thrombosis by in vivo imaging. Disease-altered uptake of pituitary and other peptide hormones can be monitored in a similar manner.

As a further example, antibodies radiohalogenated pursuant to this disclosure can be employed in in vitro radioimmunoassays.

All of the aforementioned radiohalogenated proteins are stably radiolabeled because the radiohalogen is substituted onto a nonactivated aromatic or heteroaromatic ring of the conjugate. Moreover, by thereby substituting the radiohalogen in the para or meta-position without the presence of a hydroxyl functionality, the radiohalogen is made less susceptible to catabolism by the body's deiodinase enzymes.

EXAMPLE 14

Biodistribution studies

The advantageous in vivo stability of the subject small molecule radioiodinated proteins as compared to proteins conventionally radioiodinated through a phenol-containing aromatic ring was demonstrated by the following animal experiments. In the experiments the thyroid uptake of radioiodine (as measured by neck radioactivity) was used as a measure of in vivo metabolism.

Figure 2:
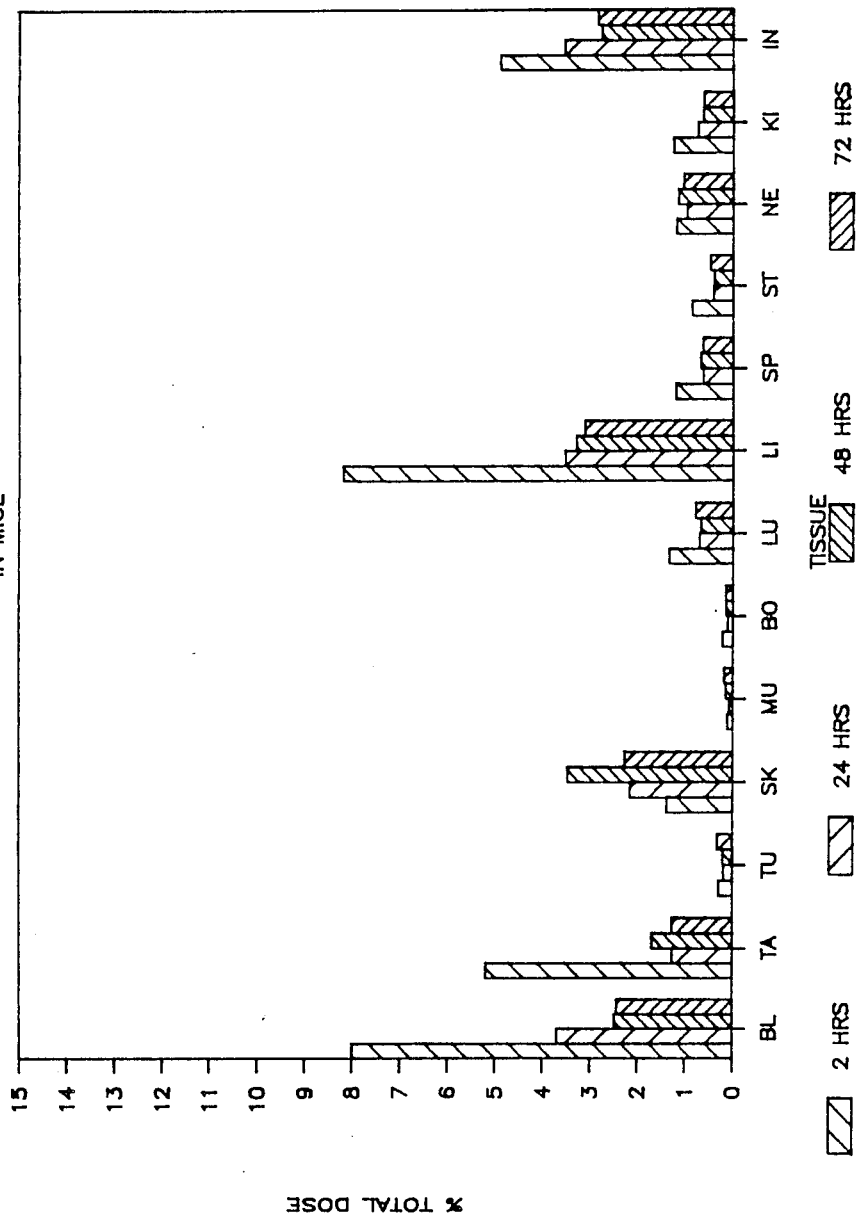

Twelve mice were injected with an antibody labeled with a radioiodinated product of Example 12. Groups of three were sacrificed at 2 hours, 24 hours, 48 hours, and 72 hours postinjection, and biodistributions of radiolabel were immediately determined by conventional techniques. The results are shown as bar graphs in FIGS. 1 and 2, in which the following symbols are used: BL, blood; TA, tail; TU, melanoma tumor; SK, skin; MU, skeletal muscle; BO, bone; LU, lung; LI, liver, SP, spleen; ST, stomach; NE, neck (including thyroid gland); KI, kidney; and IN, intestine. The results are alternatively presented as % dose/gram tissue or % total dose. (The graphs displaying % Total Dose only show a small portion of the total body activity for blood, skin, muscle, and bone.) Note that the amount of activity in the thyroid did not increase with time from the initial 2-hour baseline accumulation.

Figure 3:
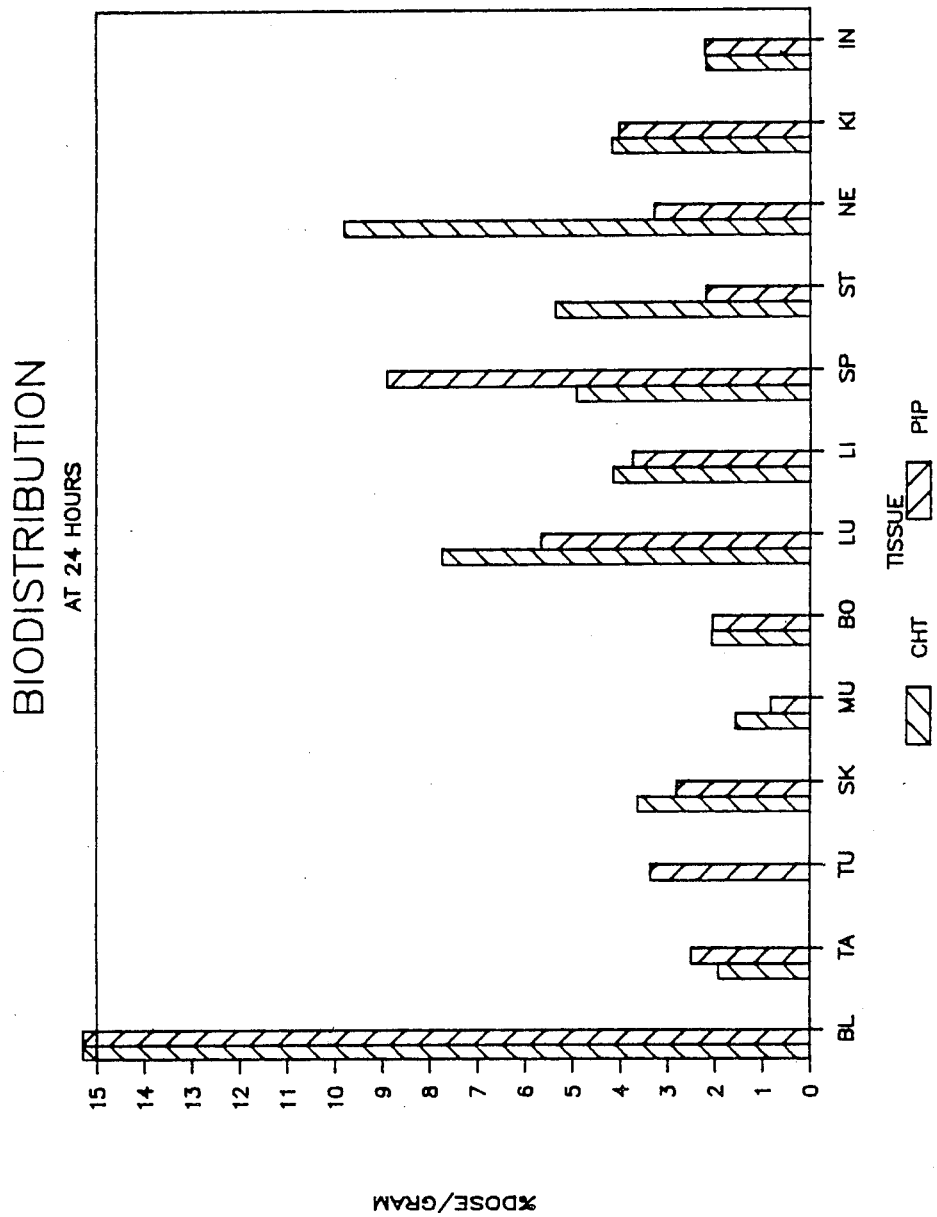
Figure 4:
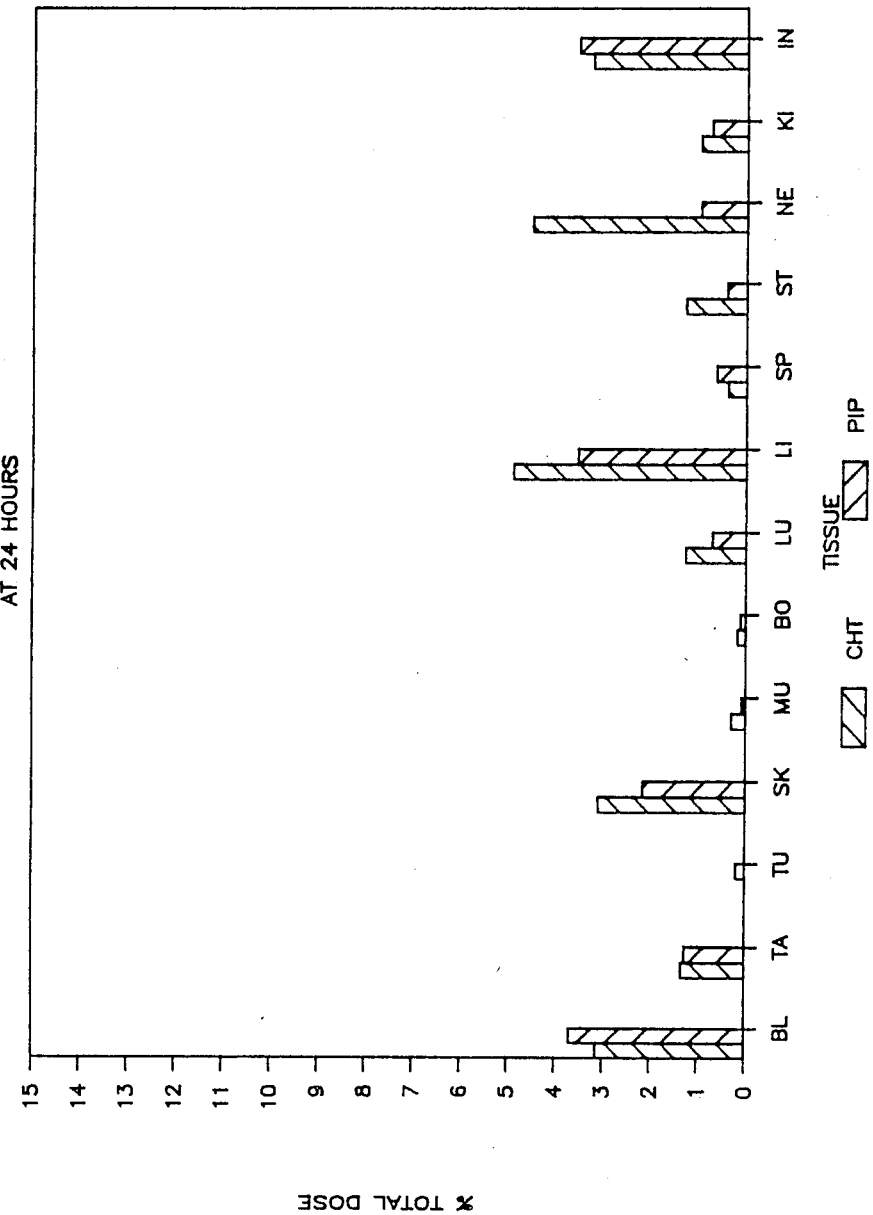

As a comparison of the stability at 24 hours, three additional mice were injected with identical amounts of the same antibody but directly labeled with radioiodine via a known chloramine-T oxidation. Biodistribution of radiolabel were determined as above, and the results are shown in FIGS. 3 and 4.

Referring to the FIGURES, at 24 hours the biodistributions of the subject and prior art reagents were very similar in the skin, bone, liver, kidney and intestine, indicating that the radiolabelled antibodies behaved similarly. In contrast, in animals injected with the chloramine-T labeled protein the stomach and neck had accumulated considerably greater fractions of the injection radioiodine, indicating that free radioiodide was most likely being produced by metabolism of the chloramine-T labeled protein. These comparative test results demonstrate that the subject para-iodophenyl-labeled antibody is much more stable in vivo, demonstrating for the first time that a nonactivated aromatic ring containing high specific activity radioiodine is not metabolically or otherwise deiodinated in vivo. The control data (FIGS. 3 and 4) is considered to be comparable to radiolabeled phenol-containing aromatic rings generally, whether labeled directly as via chloramine-T oxidation or indirectly, as with the Bolton-Hunter or Woods reagents.

Additional biodistribution studies with F(ab')$_2$ showed that antibody fragments radioiodinated by this method were stable to in vivo metabolization. Furthermore, this type of radiolabeled reagent was more rapidly cleared than the labelled whole antibody preparation discussed above, leaving minimal residue at 72 hours in the body organs.

While the present invention has been described in conjunction with a preferred embodiment, one of ordinary skill after reading the foregoing specification will be able to effect various changes, substitutions of equivalents, and other alterations to the compositions and method set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A substantially pure radiohalogenated protein produced by covalently linking a protein and a compound having the formula:

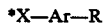

wherein

Ar is an aromatic or heteroaromatic ring;

R is a chemical bond or a substituent containing 1 to 12 straight-chain carbon atoms that does not activate Ar to electrophilic substitution on the order produced by hydroxy or amino substitution of the ring, wherein said bond or said substituent has attached thereto a functional group suitable for covalent linkage to a protein under conditions that preserve the biological activity of the protein, said functional group selected from phenolic ester, imide ester, imidate ester, anhydride, acylsuccinimide, aldehyde, isothiocyanate, thiol, diazo, amine, hydrazine, alkyl halide and maleimide; and

*X is a radioisotope of iodine, bromine, fluorine or astatine and is para- or meta-positioned relative to substituent R.

2. A method of imaging tumor cell location in the body of a mammal comprising the steps of introducing a diagnostically effective amount of the radiohalogenated protein of claim 1 into the body and thereafter scanning the body with scintillation detector means.

3. A method of tumor radiotherapy comprising the step of introducing a therapeutically effective amount of the radiohalogenated protein of claim 1 into the body of a mammal.

4. The radiohalogenated protein of claim 1, wherein Ar is phenyl.

5. The radiohalogenated protein of claim 4, wherein R is N-succinimidyl carboxylate.

6. The radiohalogenated protein of claim 4, wherein R is ethylmaleimide.

7. The radiohalogenated protein of claim 1 wherein said protein is a monoclonal antibody or fragment thereof.

8. A method of imaging tumor cell loction in the body of a mammal comprising the steps of introducing a diagnostically effective amount of the radiohalogenated protein of claim 7 into the body and thereafter scanning the body with scintillation detector means.

9. A method of tumor radiotherapy comprising the step of introducing a therapeutically effective amount of the radiohalogenated protein of claim 7 into the body of a mammal.

10. The radiohalogenated protein of claim 7 wherein said monoclonal antibody or fragment thereof is specifically reactive with a tumor cell-associated antigen.

11. A method of imaging tumor cell location in the body of a mammal comprising the steps of introducing a diagnostically effective amount of the radiohalogenated protein of claim 10 into the body and thereafter scanning the body with scintillation detector means.

12. A method of tumor radiotherapy comprising the step of introducing a therapeutically effective amount of the radiohalogenated protein of claim 10 into the body of a mammal.

13. A radiohalogenated protein composition comprising a nonradioactive protein and a radiohalogenated protein, wherein said radiohalogenated protein composition is produced by covalently linking protein molecules and a labeling composition comprising a nonradioactive compound and a compound having the formula:

$$*X-Ar-R$$

wherein
Ar is an aromatic or heteroaromatic ring;
R is a chemical bond or a substituent containing 1 to 12 straight-chain carbon atoms that does not activate Ar to electrophilic substitution on the order produced by hydroxy or amino substitution of the ring, wherein said bond or said substituent has attached thereto a functional group suitable for covalent linkage to a protein under conditions that preserve the biological activity of the protein, said functional group selected from phenolic ester, imide ester, imidate ester, anhydride, acylsuccinimide, aldehyde, isothiocyanate, thiol, diazo, amine, hydrazine, alkyl halide and maleimide; and
*X is a radioisotope of iodine, bromine, fluorine or astatine and is para- or meta-positioned relative to substituent R;
wherein said radiohalogenated protein composition has a high specific activity.

14. A method of imaging tumor cell location in the body of a mammal comprising the steps of introducing a diagnostically effective amount of the radiohalogenated protein composition of claim 13 into the body and thereafter scanning the body with scintillation detector means.

15. A method of tumor radiotherapy comprising the step of introducing a therapeutically effective amount of the radiohalogenated protein composition of claim 13 into the body of a mammal.

16. The radiohalogenated protein composition of claim 13, wherein Ar is phenyl.

17. The radiohalogenated protein composition of claim 16, wherein R is N-succinimidyl carboxylate.

18. The radiohalogenated protein composition of claim 16, wherein R is ethylmaleimide.

19. The radiohalogenated protein composition of claim 13 wherein said protein is a monoclonal antibody or fragment thereof.

20. A method of imaging tumor cell location in the body of a mammal comprising the steps of introducing a diagnostically effective amount of the radiohalogenated protein composition of claim 19 into the body and thereafter scanning the body with scintillation detector means.

21. A method of tumor radiotherapy comprising the step of introducing a therapeutically effective amount of the radiohalogenated protein composition of claim 19 into the body of a mammal.

22. The radiohalogenated protein composition of claim 19 wherein said monoclonal antibody or fragment thereof is specifically reactive with a tumor cell-associated antigen.

23. A method of imaging tumor cell location in the body of a mammal comprising the steps of introducing a diagnostically effective amount of the radiohalogenated protein composition of claim 22 into the body and thereafter scanning the body with scintillation detector means.

24. A method of tumor radiotherapy comprising the step of introducing a therapeutically effective amount of the radiohalogenated protein composition of claim 22 into the body of a mammal.

* * * * *